United States Patent [19]
Duthie et al.

[11] Patent Number: 5,808,043
[45] Date of Patent: Sep. 15, 1998

[54] COMPOSITION FOR STABILIZATION OF LABELLED NUCLEOSIDE TRIPHOSPHATES AND METHODS FOR USING SAME

[75] Inventors: R. Scott Duthie, Milwaukee; Charles K. Brush, Whitefish Bay; Eugene P. Stirchak, Brown Deer, all of Wis.; Mark E. Freeman, Middlesex, N.J.; Lawrence J. Burazin, St. Francis, Wis.

[73] Assignee: Pharmacia Biotech Inc., Milwaukee, Wis.

[21] Appl. No.: 374,456

[22] Filed: Jan. 18, 1995

[51] Int. Cl.$^6$ .............................. C07H 21/00; C07H 19/04
[52] U.S. Cl. ................. 536/25.32; 536/25.3; 536/26.41; 536/26.42; 536/26.7; 536/26.8; 435/6; 435/7.91; 435/89
[58] Field of Search .................................. 536/23.1, 25.3, 536/25.32, 25.5, 26.26, 26.7, 26.8, 26.41, 26.42; 435/6, 7.91, 89

[56] References Cited

U.S. PATENT DOCUMENTS

| 5,047,519 | 9/1991 | Hobbs, Jr. et al. ..................... 536/25.3 |
| 5,241,060 | 8/1993 | Engelhardt et al. .................... 536/25.6 |

OTHER PUBLICATIONS

Inorg. Chem., vol. 30, pp. 2130–2132 (1991).
Biochemical Journal, vol. 299, Part 3, pp. 701–709 (1994).
Newsletter of Noragen, Inc., No. 2 (1994).
Maniatis et al., Molecular Cloning, A Laboratory Manual, pp. 117–119 and 128, (1982).
F. Sanger, et al., "DNA sequencing with chain–terminating inhibitors", 74 *PNAS* 5463–5467 (1977).
P. Langer, et al., "Enzymatic Synthesis . . . Novel nucleic acid affinity probes", 78 *PNAS* 6633–6637 (1981).
L. Smith, et al., "The synthesis of oligonucleotides . . . for use in DNA sequence analysis", 13 *Nucl. Acids Res.* 2399–2412 (1985).
L. Smith, et al., "Fluorescence detection in . . . DNA sequence analysis", 321 *Nature* 674–679 (1986).
J. Prober, et al., "A System . . . with Fluorescent Chain–Terminating Dideoxynucleotides", 238 *Science* 336–341 (1987).
W. Ansorge, et al., "Automated DNA sequencing . . . fluorescent bands during electrophoresis", 15 *Nucl. Acids Res.* 4593–4602 (1987).
S. Tabor, et al., "DNA sequence analysis with . . . T7 DNA polymerase", 84 *PNAS* 4767–4771 (1987).
V. Murray, "Improved double–stranded DNA sequencing . . . ", 17 *Nucl. Acids Res.* 8889 (1989).
H. Voss, et al., "One–Step Reaction . . . Results in Uniform Labeling", 1 *Meth. Mol. Cell. Biol.* 155–159 (1990).
H. Voss, et al., "New Procedure . . . Labeling by Fluorescent dUTP", 3 *Meth. Mol. Cell. Biol.* 30–34 (1992).
H. Voss, et al., "Automated DNA Sequencing System Resolving 1,000 Bases . . . ", 3 *Meth. Mol. Cell. Biol.* 153–155 (1992).
R. Saiki, "Enzymatic Amplification of β–Globin . . . " 230 *Science* 1350–1354 (1985).
K. Mullis, et al., "Specific Enzymatic Amplification of DNA in Vitro . . . ", 51 *Cold Spring Harbor Symp. Quant. Biol.* 263–273 (1986).
*P–L Analects*, P–L Biochemicals, Inc., vol. 9, No. 4, pp. 1 and 4 (1981).
*Analects*, Pharmacia Biotech Inc., vol. 22, No. 1, p. 8 (1993).
P. 72 from Boehringer Mannheim Biochemicals Catalog (1993).
R.M. Dawson, et al., Eds., *Data for Biochemical Research*, 3d Edition, Clarendon Press, Oxford, pp. 399–415 (1986).

*Primary Examiner*—James O. Wilson
*Attorney, Agent, or Firm*—Quarles & Brady

[57] ABSTRACT

A preparation of a labelled nucleotide comprising at least one compound having a $Mg^{2+}$ association constant between $1\times10^{-11}$ to $1\times10^{-2}$, inclusive. The compound is preferably selected from the group consisting of citrate, isocitrate, phosphate, EGTA, EDTA, and CDTA. The concentration of the compound is preferably at least 5 mM.

17 Claims, 6 Drawing Sheets

COMPOSITION FOR STABILIZATION OF LABELLED NUCLEOSIDE TRIPHOSPHATES AND METHODS FOR USING SAME

BACKGROUND OF THE INVENTION

1. Field of the Invention

In general, the field of the present invention is stabilized preparations of labelled nucleoside triphosphates. Specifically, the field of the present invention is labelled nucleoside triphosphates stored in a buffer comprising citrate, isocitrate, EGTA, EDTA, and/or CDTA.

2. Background of the Art

DNA sequencing is generally accomplished by the method of Sanger, et al. (*Proc. Natl. Acad. Sci. USA*. vol. 74, 1977, pp. 5463–5467) and involves the in vitro enzymatic synthesis of single-stranded DNA starting from either a single- or double-stranded DNA template. In the original embodiment of the sequencing protocol, a primer, usually a synthetic oligonucleotide 15 to 30 bases in length, was first annealed to its complementary sequence on the template of the single-stranded DNA to be sequenced.

The 3'-end of this primer was extended by the Klenow fragment of *E. coli* DNA polymerase I in the presence of 2'-deoxynucleoside 5'-triphosphates (dNTPs), one of which contained a radiolabel. Four separate sequencing reactions were performed, each buffered reaction containing all four dNTPs (2'-deoxyadenosine 5'-triphosphate (dATP), 2'-deoxycytidine 5'-triphosphate (dCTP), 2'-deoxyguanosine 5'-triphosphate (dGTP), and 2'-deoxythymidine 5'-triphosphate (dTTP)), and a small amount of one specific 2',3'-dideoxynucleoside 5'-triphosphate chain-terminating agent (either ddATP, ddCTP, ddGTP, or ddTTP; or, in general, ddNTP).

By varying the ratio of the specific chain-terminating ddNTP to its dNTP analog in a particular reaction, the polymerase generated a population of fragments where a specific ddNTP had been substituted at every possible position along the DNA template where the corresponding dNTP would have been incorporated. Once the one-step labelling and termination step had been completed, an excess of all four dNTPs was added to each reaction to "chase" all fragments not terminated by a specific ddNTP into higher molecular weight DNA. The products of the four separate reactions were then fractionated in adjacent lanes on a high resolution denaturing polyacrylamide gel system. Visualization of the separated DNA fragments was accomplished by exposing the gel to X-ray film and subsequently developing the film. Each band on the autoradiogram corresponded to its specific complementary nucleotide base in the sequence of the DNA template in a 5' (bottom of the autoradiogram) to 3' (top of the autoradiogram) direction from the primer.

In 1987 Tabor and Richardson (Tabor, S. and C. C. Richardson. *Proc. Natl. Acad. Sci. USA*. vol. 84, 1987, pp. 4767–4771) described a modification of the basic Sanger protocol for use with T7 DNA polymerase that separated the labelling from the termination step. T7 DNA polymerase and a limiting amount of all four dNTPs, one of which was radiolabelled, were added to an annealed template and primer. During a short incubation step at a suboptimal polymerization temperature (room temperature) the polymerase added one to several hundred dNTPs to the 3'-end of the primer, while also incorporating the radiolabelled dNTP in all of the extended fragments. At the end of the labelling step, the mixture was aliquoted equally into four separate termination reactions. Each termination reaction contained nonlimiting concentrations of all four dNTPs and one specific ddNTP. Following a second short incubation step at the optimal polymerization temperature for the polymerase (37° C.), detection of the DNA fragments was done as outlined for the Sanger protocol. The final process in both of the radiolabelled sequencing protocols described above included reading the autoradiogram to generate an ordered DNA sequence and then manual entry of this sequence into a data base for subsequent manipulations.

Murray (Murray, V. *Nucl. Acids Res.* vol. 17, 1989, p. 8889) described a novel method for sequence generation from DNA templates with ddNTP termination of DNA fragments. Murray used a variation of the polymerase chain reaction (Mullis, K. B., et al. *Cold Spring Harbor Symp. Quant. Biol.* vol. 51, 1986, pp. 263–273; Saiki, R. K., et al. *Science* vol. 230, 1985, pp. 1350–1354) termed "cycle sequencing." Cycle sequencing uses a small amount of template DNA combined with an excess of one primer, dNTPs, a radiolabelled dNTP, ddNTPs and a thermostable DNA polymerase. The mixture undergoes 20 to 30 cycles of thermal cycling, each cycle consisting of a denaturation, an annealing and a polymerization step. Denaturation temperatures typically are 94° C.–95° C., while annealing temperatures are calculated according to the melting temperature between the primer and its complementary sequence on the DNA template (usually between 37° C. and 72° C.). Polymerization temperatures are picked to be optimal for the thermostable polymerase used in the reaction. The handling of completed cycle sequencing reactions, as with the two other methods mentioned above, includes gel electrophoresis, data entry and manipulation.

Since the mid-1980's automated DNA sequencing instruments have automated the gel electrophoresis, data collection, sequence generation and data entry steps involved with the radiolabelled methods described above. These automated instruments have taken advantage of certain dyes that emit photon energy when excited with a laser, eliminating the need to use radioactivity to detect the separated DNA fragments. All of the instruments incorporate a high resolution polyacrylamide gel system for separation of the labelled DNA fragments. Each instrument also contains some form of detection system at a point across the length of the gel near its bottom to detect the fluorescently-labelled fragments as they migrate during electrophoresis.

Currently, commercially available automated instruments are based upon the detection technologies of: (1) single fluorescent-labelled primers or dNTPs with the sequencing reactions run and detected in separate lanes of a gel (Ansorge, W., et al. *Nucl. Acids Res.* vol. 15, 1987, pp. 4593–4602), (2) primers labelled with four separate fluors (Smith, L., et al. *Nucl. Acids Res.* vol 13, 1985, pp. 2399–2412; Smith, L., et al. *Nature* vol 321, pp. 674–679) allowing all four reactions to be run and detected in one lane on a gel, or (3) the same strategy as in (2), except with the substitution of four different fluorescently-labelled ddNTPs for the labelled primers (Prober, J., et al. *Science* vol. 238, 1987, pp. 336–341).

Sequencing reactions for use with AUTOMATED LASER FLUORESCENT (ALF) DNA Sequencer (Pharmacia Biotech Inc.) contain a single fluorescein label attached either to a primer or to a dNTP molecule for generation and collection of sequence data. When a fluorescein-labelled primer is used in the reactions, sequences may be generated using methodologies employing both T7 DNA polymerase and cycle sequencing, as basically described above. Both methodologies are readily adaptable for use with a labelled primer instead of a radiolabelled dNTP. In addition, the T7 reaction can be modified slightly to provide both primer extension (labelling) and termination in a single step (Voss, H., et al. *Meth. Mol. & Cell. Biol.*, vol. 1, 1989, pp. 155–159) without the need for a chase step to remove nonspecifically terminated fragments. It is also possible to internally label the fragments using either fluorescein-12-dUTP (2'-deoxyuridine 5'-triphosphate) or fluorescein-15-dATP in combination with an unlabelled-primer (Voss, H., et al. *Meth. Mol. & Cell. Biol.*, vol. 3, 1992, pp. 30–34; Voss, H., et al. *Meth. Mol. & Cell. Biol.*, vol. 3, 1992, pp. 153–155, respectively). At present, there are commercial products available for all of the sequencing methodologies discussed above for use with ALF DNA Sequencer (Pharmacia Biotech Inc.).

The commercially available labelling mix containing fluorescein-15-dATP (FIG. 1) for use with T7 DNA polymerase (Fluore-dATP Labelling Mix; Pharmacia Biotech Inc.) contained a fluorescent breakdown product that seriously affected data collection 40 to 50 bases into the sequence (FIG. 2). This fluorescent breakdown product regularly obscured five to seven bases of sequence data and caused the researcher using this sequencing methodology to expend extra time, effort and money to obtain the lost sequence.

There are several issues that historically have been associated with stability and purity of dNTPs. During their synthesis, purity of the starting material, in terms of the oxidation state of the sugar moiety (i.e., contaminating mixtures of D-ribose, 2'-deoxy-D-ribose and 2',3'-dideoxy-D-ribose), was critical (P-L Analects, *P-L Biochemicals, Inc.* vol. 9 no. 4, 1981, pp. 1 & 4). Additionally, storage of the synthesized and purified dNTPs was in solid form at –76° C. However, storage of lyophilized dNTPs was still unstable when the solid was allowed to warm to room temperature. Highly purified lyophilized dNTPs were susceptible to disproportionation, giving rise to 1%–2% diphosphate per day when held at room temperature (P-L Analects, *P-L Biochemicals, Inc.* vol. 9 no. 4, 1981, pp. 1 & 4) or exhibiting decomposition in the range of 4%–10% within 6 months when stored in solution at –20° C. (Boehringer Mannheim Corp., 1993 Catalog, p. 72).

It is now recognized that dNTPs in solution are not as susceptible to disproportionation (a concentration-dependent reaction) as the lyophilized forms and are also more stable upon prolonged storage at –20° C. (>99% triphosphate even after 30 months of storage; Analects, *Pharmacia Biotech Inc.* vol. 22 no. 1, 1993, p.8). Stability was still not an issue with the advent of nonisotopically-labelled dNTPs in the early 1980s (Langer, P. R., et al., *Proc. Natl. Acad. Sci. USA* vol. 78, 1981, pp. 6633–6637). The types of reactions using these compounds usually involved some form of purification or washing step prior to visualization of the final product (e.g., hybridizations). Not until the use of fluorescein-labelled dNTPs in the early 1990s for the automated visualization of sequencing reactions did the stability of dNTP solutions became critical.

What the art of DNA sequencing requires is a method to stabilize labelled nucleoside triphosphates, so that breakdown products which are detrimental to detection of sequencing fragments are prevented from forming upon storage in dilute solution.

SUMMARY OF THE INVENTION

We have discovered a preparation of labelled nucleoside triphosphates which exhibits surprising stability and avoids the detrimental breakdown products of the prior art. One version of the stabilized preparation of a labelled nucleotide comprises at least one compound having a $Mg^{2+}$ association constant between $1\times10^{-11}$ to $1\times10^{-2}$, inclusive and a concentration of at least 5 mM.

The labelled nucleotide preferably has the formula PM-SM-BASE-SIG wherein PM is a phosphate moiety, SM is a sugar moiety, BASE is a pyrimidine, purine or 7-deazapurine moiety, PM being attached at the 3' or the 5' position of SM when the nucleotide is a deoxyribonucleotide and at the 2', 3' or 5' position when the nucleotide is a ribonucleotide, BASE being attached to the 1' position of SM from the $N^1$ position when BASE is a pyrimidine or the $N^9$ position when BASE is a purine or a 7-deazapurine, and SIG is covalently attached to BASE and wherein SIG represents a detectable moiety.

Preferably the at least one compound is selected from the group consisting of citrate, isocitrate, phosphate, EGTA, EDTA, and CDTA.

SIG is preferably selected from the group consisting of fluorophores, chromophores, and radiolabels. SIG is more preferably selected from the group consisting of fluoresceins, carbocyanines, and rhodamines.

SIG can be a fluorescein and, thus, the labelled nucleotide can be fluorescein-labelled dATP.

SIG can be a carbocyanine and, thus, the labelled nucleotide can be carbocyanine-labelled dATP.

The labelled nucleotide can be covalently attached to at least one nucleoside.

The compound is preferably a carboxylic acid or a compound having at least one carboxylic acid group.

Another version of the invention provides a method of stabilizing a labelled nucleotide comprising the step of adding to the labelled nucleotide at least one compound having a $Mg^{2+}$ association constant from $1\times10^{-11}$ to $1\times10^{-2}$, wherein the final concentration of the compound is at least 5 mM. The method preferably comprises the further step of first removing pyrogens from the constituents. Filtering is preferably used to remove the pyrogens.

Another version of the invention provides a method of using the above preparation comprising incubating the preparation in the presence of a DNA polymerase, a RNA polymerase, or a reverse transcriptase.

In another aspect, the labelled nucleotide is fluorescein-15-dATP. In this aspect, the most preferred to least preferred buffers for F-dATP stock solutions are EGTA >citrate pH 7.7=EDTA=CDTA=isocitrate pH 7.7>isocitrate pH 6.4= citrate pH 6.6>phosphate>$dH_2O$ while the most preferred to least preferred buffers for dilute F-dATP labelling mixes are citrate pH 7.7=EGTA=isocitrate pH 7.7>CDTA>citrate pH 6.6>EDTA>isocitrate pH 6.4>phosphate>$dH_2O$.

In another aspect, the labelled nucleotide is carbocyanine-13-dATP. In this aspect, the most preferred to least preferred buffers for carbocyanine-dATP stock solutions are CDTA>EGTA>EDTA=isocitrate pH 6.4>phosphate>isocitrate pH 7.7>citrate pH 7.7>citrate pH 6.6>$dH_2O$ while the most preferred to least preferred buffers for dilute carbocyanine-dATP labelling mixes are EDTA>isocitrate pH 7.7>isocitrate pH 6.4>CDTA=citrate pH 7.7=citrate pH 6.6>EGTA>phosphate>$dH_2O$. The concentration of the buffers in each preparation above is at least 5 mM, preferably at least 50 mM.

The objects of the invention, therefore, include providing preparations of labelled nucleotides of the above kind which:

(a) avoid detrimental breakdown products that interfere with DNA sequencing;

(b) stabilize labelled dNTPs during PCR;

(c) stabilize labelled primers during PCR;

(d) stabilize dNTPs during lyophilization; and (e) prevent depurination of labelled molecules.

These and still other objects and advantages of the present invention will be apparent from the description below. However, this description is only of the preferred embodiments. The claims should, therefore, be looked to in order to assess the whole scope of the invention.

DETAILED DESCRIPTION OF THE INVENTION

Figure 1:
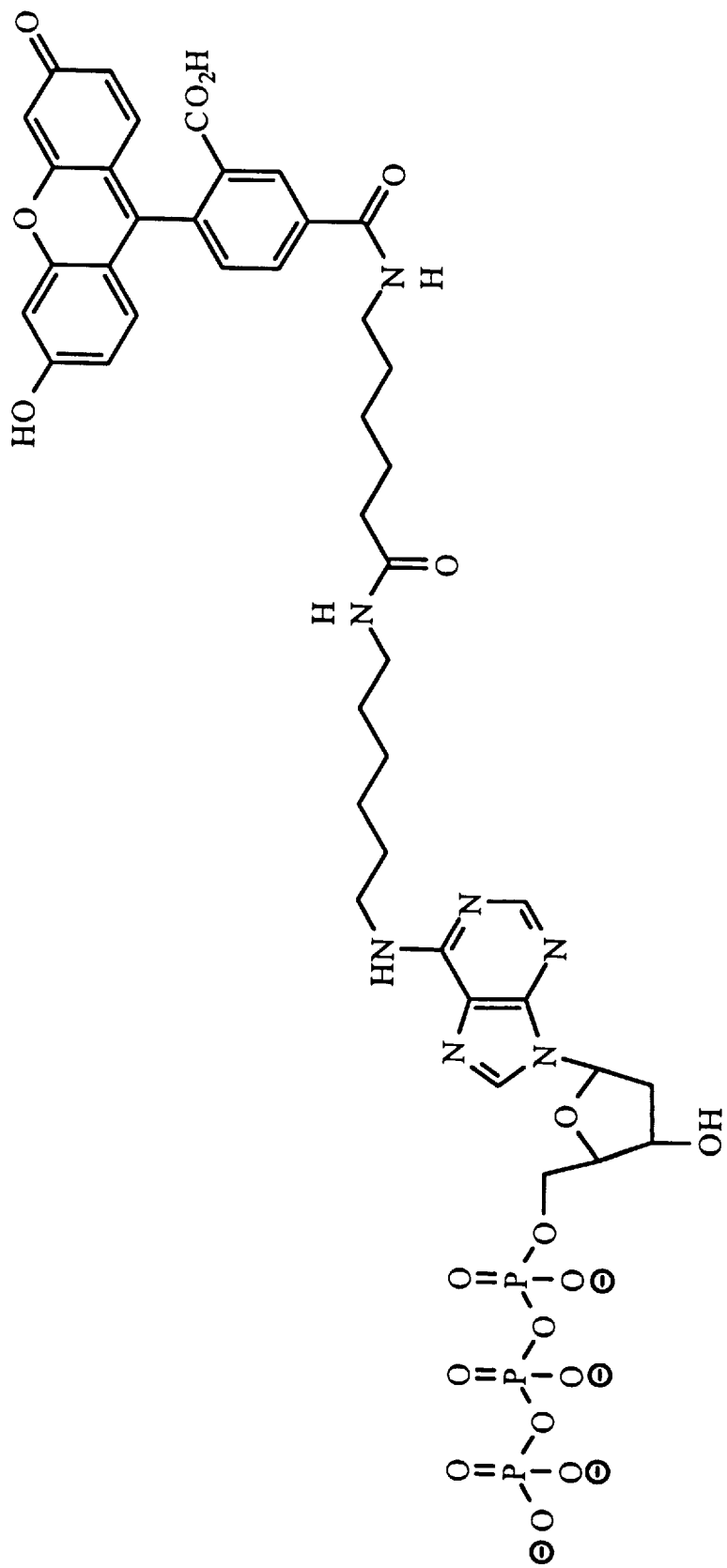
FIG. 1 shows the structure of fluorescein-15-dATP.
Figure 2:
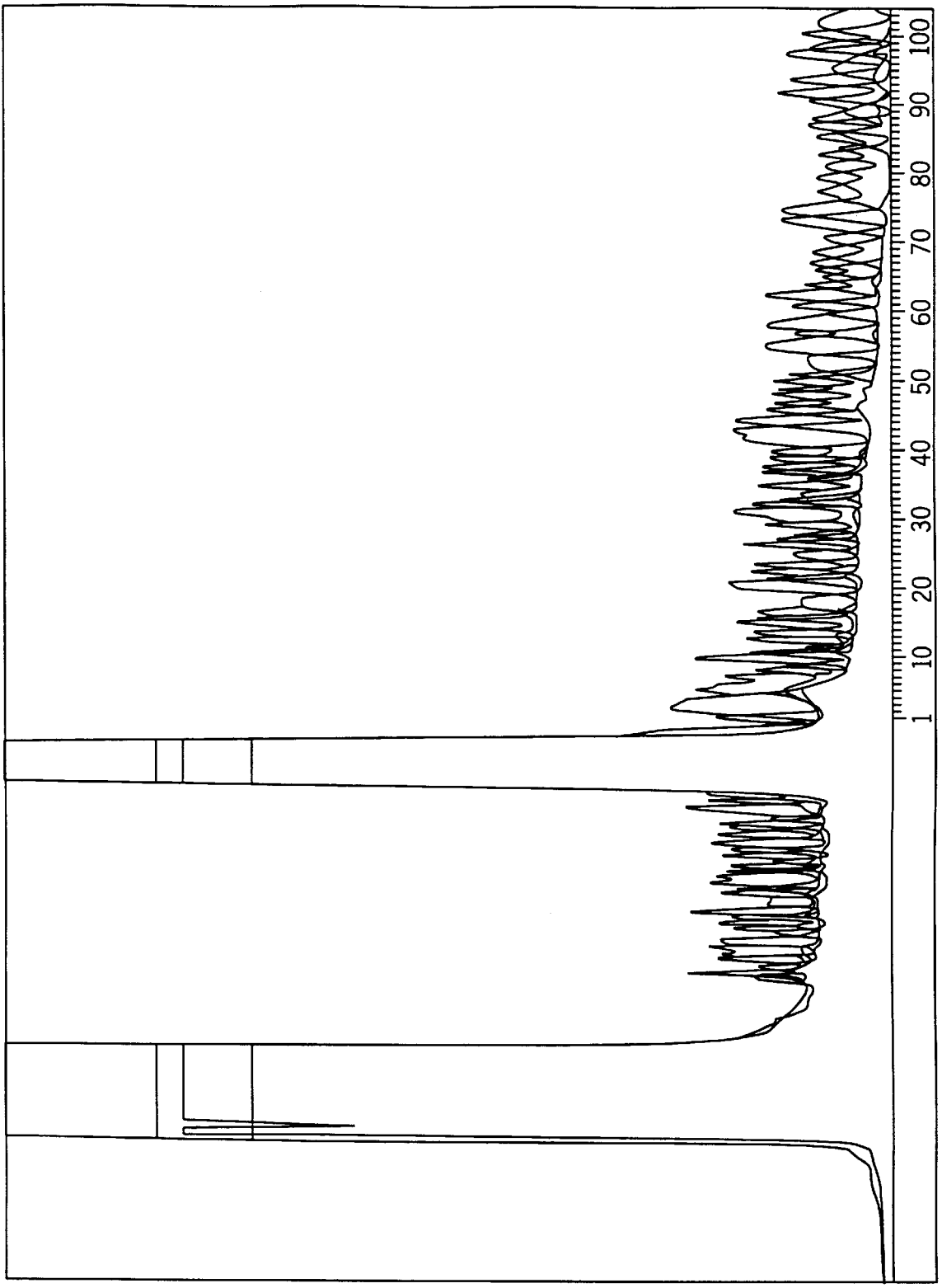
FIG. 2 shows the depurination product of fluorescein-15-dATP which obscures sequence data.
Figure 2A:
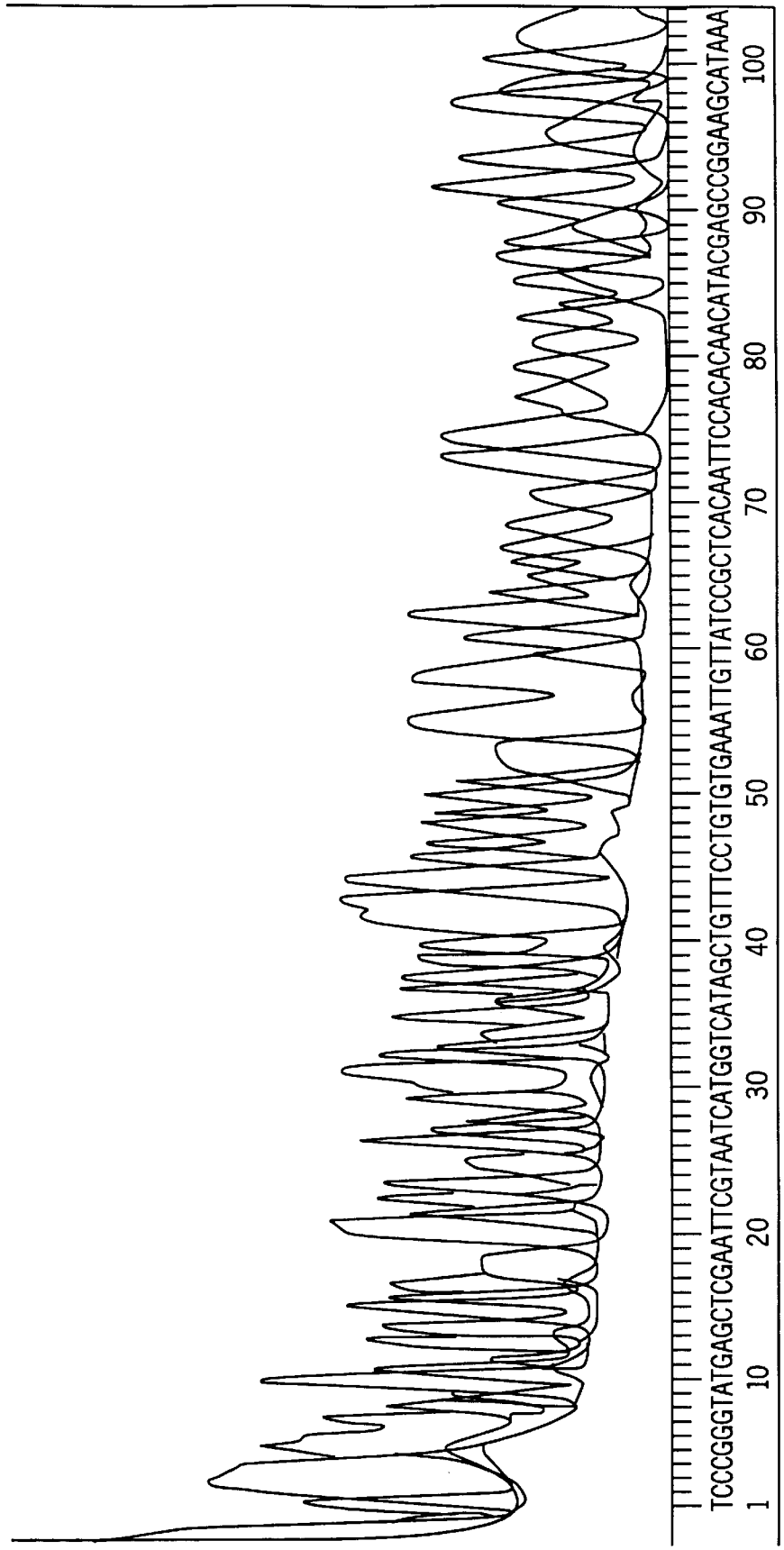
Figure 3:
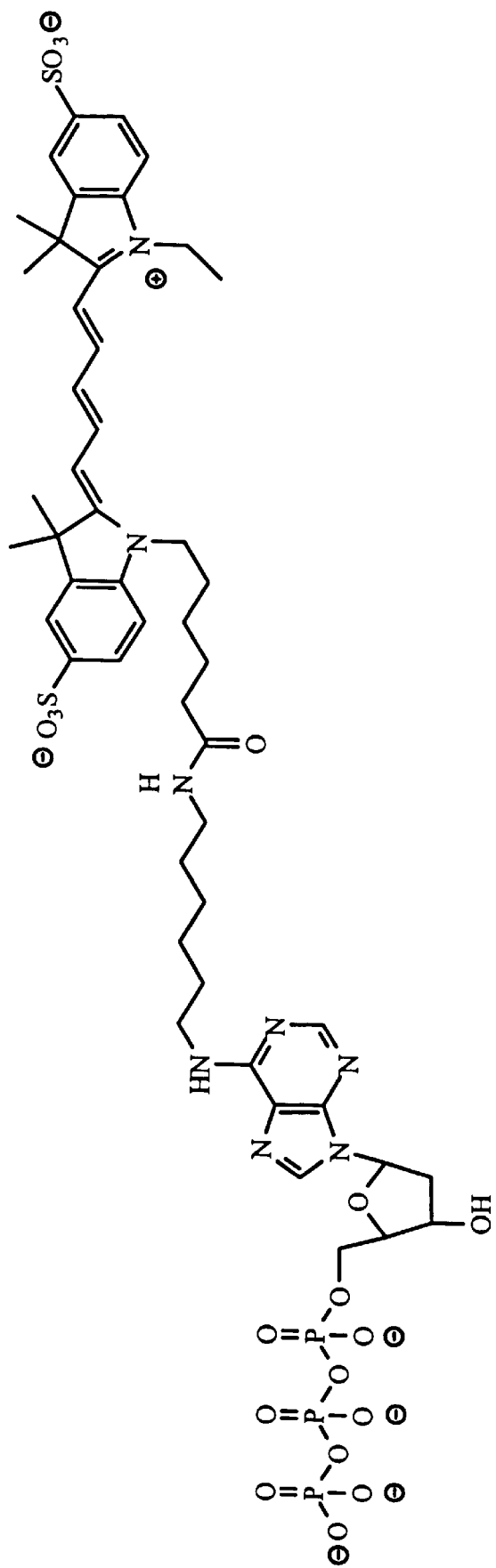
FIG. 3 shows the structure of carbocyanine 13-dATP.
Figure 4:
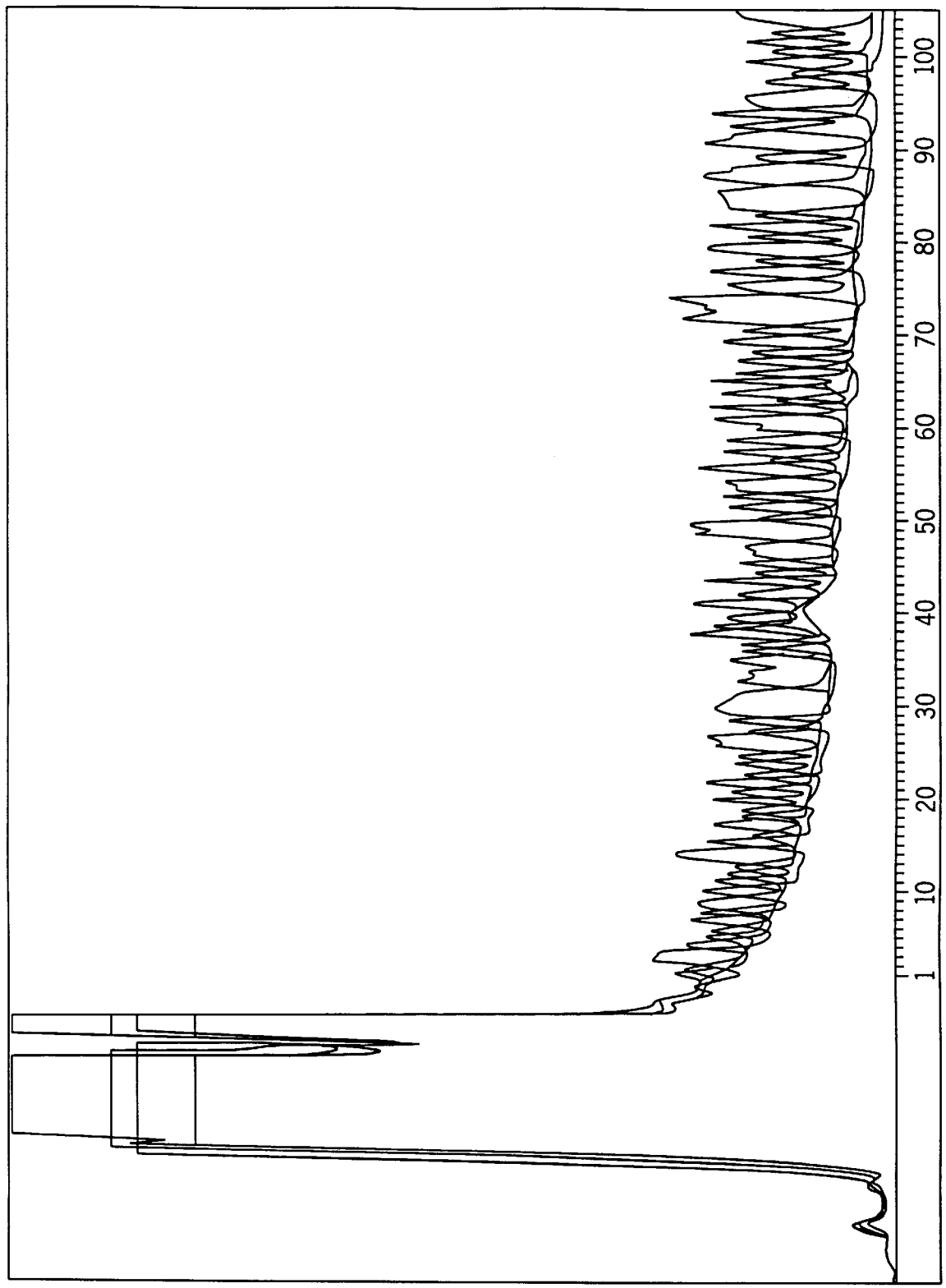
FIG. 4 shows the sequencing results using F-dATP stabilized in 50 mM citrate, pH 7.7.
Figure 4A:
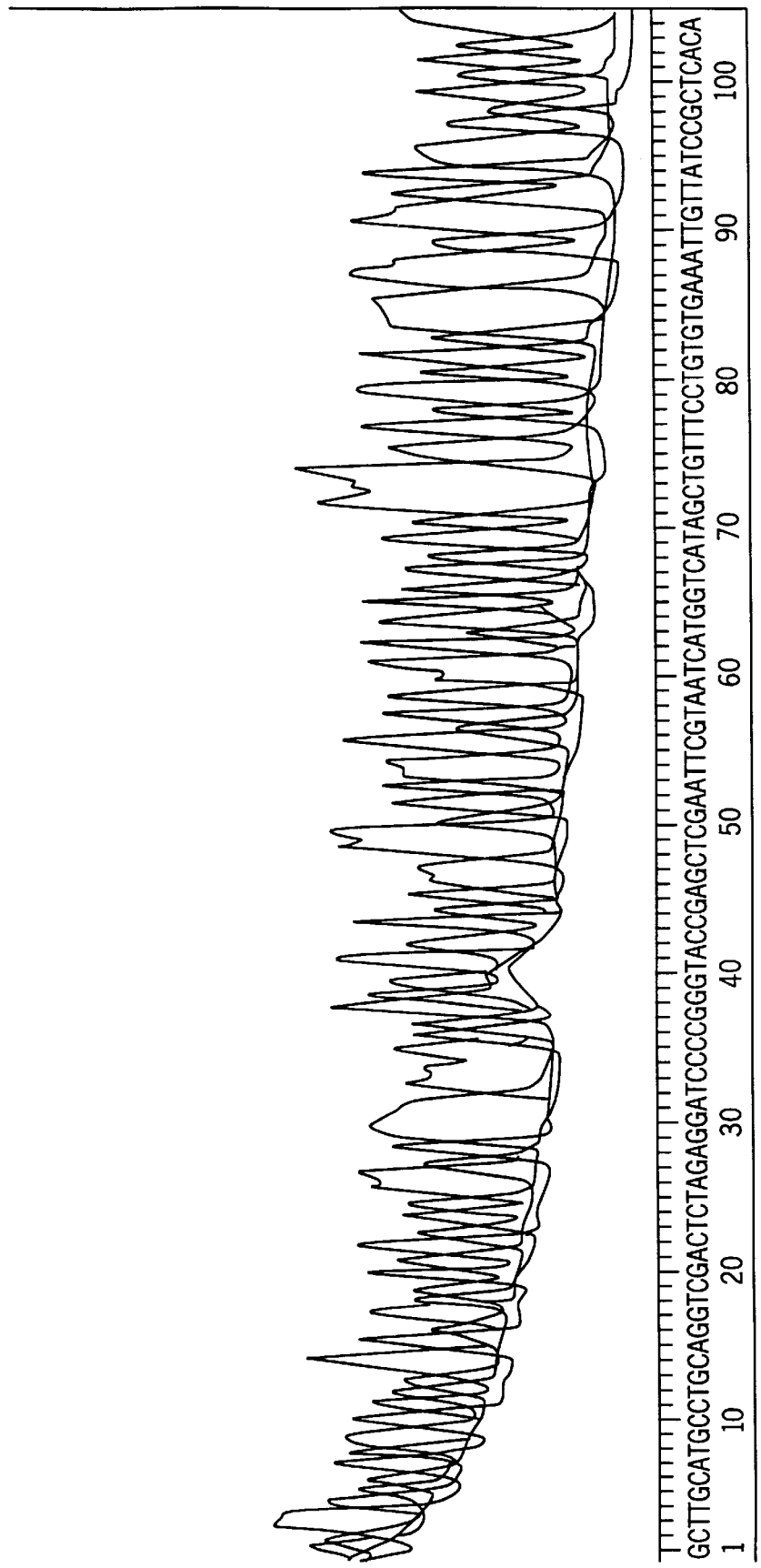

In one aspect the invention discloses a way to stabilize fluorescein-15-dATP (F-dATP) during storage in solution to prevent depurination of the molecule. This stabilization method is readily incorporated into the T7 sequencing reactions and does not appear to have a detrimental effect upon the polymerase's ability to generate sequence data.

In another embodiment, the present invention is a method and composition for storage of solutions containing Cy5-13-dATP (carbocyanine-13-dATP) (Biological Detection Systems, Inc.) used in T7 sequencing reactions with another commercially available automated DNA sequencing instrument, ALFRED DNA Sequencer (Pharmacia Biotech Inc.). The present invention is also useful for stabilizing labelled dNTP for use during PCR reactions, labelled primers, labelled dNTPs during lyophilization, labelled ddNTPs, and rNTPs.

EXAMPLES

The following examples are offered by way of illustration and not by way of limitation.

All temperatures are in degrees centigrade (25° refers to ambient or room temperature). The following abbreviations are employed: EGTA (ethylene glycol-bis-(β-amino-ethyl ether) N,N,N',N'-tetraacetic acid); EDTA (ethylenediaminetetraacetic acid); CDTA (trans-1,2-diaminocylohexane-N, N,N',N'-tetraacetic acid); dH$_2$O (sterile distilled water); mM (millimolar); μM (micromolar); F-dATP (fluorescein-15-dATP); FPLC (Fast Protein Liquid Chromatography); d (daltons).

By Mg$^{2+}$ association constant (stability constant) we mean as defined and determined in the following references: *Stability constants of metal-ion complexes* (1964), compiled by L. G. Sillén, et al., Special Pub. No. 17, The Chemical Society, London; *Stability constants of metal-ion complexes, Supplement* No. 1 (1971), compiled by L.G. Sillén, et al., Special Pub. No. 25, The Chemical Society, London; *Stability constants of metal-ion complexes: organic ligands* (1979), compiled by D. D. Perrin, Pergamon Press, Oxford; F. Rossotti, et al., *The determination of stability constants*, McGraw-Hill, New York (1961); and *Data for Biochemical Research*, 3d Edition (1986), R. Dawson et al. (Eds), Clarendon Press, Oxford.

The Mg$^{2+}$ association constant for citrate is $1\times10^{-3.6}$, for isocitrate is $1\times10^{-2.6}$, for CDTA is $1\times10^{-11}$, for EDTA is $1\times10^{-8.7}$, for EGTA is $1\times10^{-5.2}$. By detectable moiety, we mean, for example, any fluorescing moiety, biotin, radiolabel, magnetic label, antibody, etc. By fluorescing moiety we mean, for example, fluorophores and chromophores. Preferred compounds for the stabilized preparation are those having at least one carboxylic acid group.

The electrophoresis plots of the various samples in examples 1, 2, 4, 5, and 6 were qualitatively and comparatively analyzed by assigning "+" signs (or"−" as the case may be) based on the width and height of the contaminant (disproportionation and depurination) peaks. Each "+" signifies a greater degree of stabilization. By stability, we mean as compared to the solution held at −20° C. All buffers were compared to the stability of the labelled nucleotides in citrate pH 7.7 which was arbitrarily given a value of three "+"s (+++).

EXAMPLE 1

As shown below in Table 1, stock solutions of F-dATP were prepared in the listed buffers at the indicated pH and concentrations. Aliquots from each F-dATP stock were stored at +50° for three days; identical aliquots were also stored at −20° for three days. At the end of this period each aliquot was diluted to 0.3 μM using the appropriate buffer or dH$_2$O. Storage at 50° is meant to be an accelerated stability test.

Seven μl of the diluted samples were then mixed with 5 μl of gel loading dye (~100% deionized formamide containing 5 mg/ml Blue Dextran 2000) and 8 μl of the resulting solution was loaded into wells of a sequencing gel. The samples were electrophoresed using AUTOMATED LASER FLUORESCENT (ALF) DNA Sequencer. Plots from the electrophoresis of each of these solutions were evaluated and tabulated below in Table 1.

These results demonstrate the effectiveness of the buffers as follows: EGTA>citrate pH 7.7=EDTA=CDTA=isocitrate pH 7.7 >isocitrate pH 6.4=citrate pH 6.6>phosphate>dH$_2$O.

TABLE 1

| Buffer | pH | F-dATP Stock Concentration | Stability |
| --- | --- | --- | --- |
| 50 mM Citrate | 7.7 | 0.50 mM | +++ |
| 50 mM Citrate | 6.6 | 0.43 mM | ++ |
| 50 mM EGTA | 7.8 | 0.43 mM | ++++ |
| 50 mM EDTA | 7.6 | 0.43 mM | +++ |
| 50 mM CDTA | 7.7 | 0.43 mM | +++ |
| 50 mM isocitrate | 7.7 | 0.40 mM | +++ |
| 50 mM isocitrate | 6.4 | 0.43 mM | ++ |
| 50 mM phosphate | 7.0 | 0.43 mM | + |
| Sterile dH$_2$O | ~5.5 | 0.43 mM | − |

EXAMPLE 2

Each of the F-dATP stock solutions from Example 1 (those stored at −20° C.) were diluted to prepare a labelling mix for use with T7 DNA polymerase according to the following formulation:

| Component | Concentration |
| --- | --- |
| F-dATP | 10.0 μM |
| dCTP | 1.0 μM |
| dGTP | 1.0 μM |
| dTTP | 1.0 μM |
| Appropriate Buffer | 50 mM |

The identical buffer used to prepare the concentrated stock of F-dATP was used to prepare the labelling mix, except in the case where dH$_2$O was used. Aliquots of the labelling mixes were also incubated at either +50° or −20° C. for three days (as in Example 1). After the incubation period the labelling mixes were diluted 1:31 using the appropriate buffer or dH$_2$O. 7 µl of the diluted labelling mixes were then mixed with 5 µl of gel loading dye and 8 µl of the resulting solution was loaded into appropriate wells of a sequencing gel. Plots from the electrophoresis of each of these solutions demonstrate the effectiveness of the buffers as follows: citrate pH 7.7=EGTA=isocitrate pH 7.7>CDTA>citrate pH 6.6>EDTA>isocitrate pH 6.4>phosphate>dH$_2$O. In addition, each of the labelling mixes was used to generate a DNA sequence with T7 DNA polymerase, AUTOREAD Sequencing Kit (Pharmacia Biotech Inc.), an unlabelled primer and M13mp18(+) strand as the DNA template. The results of the DNA sequencing reactions mirror the results of the electrophoresis plots above.

The results are summarized below in Table 2.

TABLE 2

| Buffer | pH | Stability of F-dATP Labelling Mix |
|---|---|---|
| 50 mM Citrate | 7.7 | +++ |
| 50 mM Citrate | 6.6 | + |
| 50 mM EGTA | 7.8 | +++ |
| 50 mM EDTA | 7.6 | − |
| 50 mM CDTA | 7.7 | ++ |
| 50 mM isocitrate | 7.7 | +++ |
| 50 mM isocitrate | 6.4 | −− |
| 50 mM phosphate | 7.0 | −−− |
| Sterile dH$_2$O | ~5.5 | −−−− |

EXAMPLE 3

100 mM stocks of dATP, dCTP, dGTP and dTTP were diluted to 90 mM using 1M citrate stocks of different pHs: pH 4.5, pH 6.5 or pH 7.5. The final concentration of citrate in all of the dilutions was 100 mM. All of the samples were lyophilized over the course of 20 hours using a temperature gradient of −40° to +16°. Once dried, all of the samples were resuspended in dH$_2$O and analyzed by FPLC using a MONO Q column with a sodium chloride gradient at pH 7.5. Integrated values for the lyophilized dNTPs and the disproportionation products are summarized below in Table 3.

These results show that these solutions maintain good stability against disproportionation through the lyophilization process.

TABLE 3

| | dNTP | % (PO$_4$)$_3$ | % (PO$_4$)$_2$ | % (PO$_4$)$_4$ |
|---|---|---|---|---|
| pH 4.5 | dATP | 98.2 | 1.4 | 0.1 |
| | dCTP | 98.8 | 1.1 | 0.0 |
| | dGTP | 97.8 | 1.3 | 0.5 |
| | dTTP | 97.4 | 1.1 | 1.4 |
| pH 6.5 | dATP | 95.7 | 3.0 | 0.9 |
| | dCTP | 95.7 | 3.0 | 1.1 |
| | dGTP | 95.8 | 2.5 | 1.2 |
| | dTTP | 92.5 | 4.6 | 2.0 |
| pH 7.5 | dATP | 92.9 | 4.6 | 2.5 |
| | dCTP | 89.5 | 7.1 | 2.6 |
| | dGTP | 91.8 | 5.5 | 2.7 |
| | dTTP | 94.3 | 3.5 | 1.8 |

EXAMPLE 4

As shown below in Table 4, stock solutions of Cy5-dATP were prepared in the listed buffers at the indicated pH and concentrations. In addition, the appropriate buffers or dH$_2$O used for this example were also filtered through a membrane with a molecular cutoff of 10,000 d (CENTRIPREP-10, Amicon, Inc.).

Aliquots from each Cy5-dATP stock were either stored at +50° or −20° for three days (as in Example 1). At the end of this period each aliquot was diluted to 0.3 µM using the appropriate buffer or dH$_2$O. Seven µl of the diluted samples were then mixed with 5 µl of gel loading dye and 8 µl of the resulting solution was loaded into wells of a sequencing gel. The samples were electrophoresed using ALFRED DNA Sequencer (Pharmacia Biotech Inc.). Plots from the electrophoresis of each of these solutions were analyzed and tabulated below in Table 4.

These results demonstrate the effectiveness of the buffers as follows: CDTA>EGTA>EDTA=isocitrate pH 6.4>phosphate>isocitrate pH 7.7>citrate pH 7.7>citrate pH 6.6 >dH$_2$O.

TABLE 4

| Buffer | pH | Cy5-dATP Stock Concentration | Stability |
|---|---|---|---|
| 50 mM Citrate | 7.7 | 0.50 mM | +++ |
| 50 mM Citrate | 6.6 | 0.50 mM | ++ |
| 50 mM EGTA | 7.8 | 0.50 mM | +++++++ |
| 50 mM EDTA | 7.6 | 0.50 mM | ++++++ |
| 50 mM CDTA | 7.7 | 0.50 mM | ++++++++ |
| 50 mM isocitrate | 7.7 | 0.50 mM | ++++ |
| 50 mM isocitrate | 6.4 | 0.50 mM | ++++++ |
| 50 mM phosphate | 7.0 | 0.50 mM | +++++ |
| Sterile dH$_2$O | ~5.5 | 0.50 mM | − |

EXAMPLE 5

Each of the Cy5-dATP stock solutions from Example 4 (those stored at −20° C.) were diluted to prepare a labelling mix for use with T7 DNA polymerase according to the following formulation:

| Component | Concentration |
|---|---|
| Cy5-dATP | 10.0 µM |
| dCTP | 1.0 µM |
| dGTP | 1.0 µM |
| dTTP | 1.0 µM |
| Appropriate Buffer | 50 mM |

The identical buffer used to prepare the concentrated stock of Cy5-dATP was used to prepare the labelling mix, except in the case where dH$_2$O was used. Aliquots of the labelling mixes were also incubated at either +500° or −20° C. for three days (as in Example 1). After the incubation period the labelling mixes were diluted 1:31 using the appropriate buffer or dH$_2$O. 7 µl of the diluted labelling mixes were then mixed with 5 µl of gel loading dye and 8 µl of the resulting solution was loaded into wells of a sequencing gel. Plots from the electrophoresis of each of these solutions were analyzed and demonstrate that the effectiveness of the buffers is as follows: EDTA>isocitrate pH 7.7>isocitrate pH 6.4>CDTA=citrate pH 7.7=citrate pH 6.6>EGTA>phosphate>dH$_2$O. In addition, each of the labelling mixes was used to generate a DNA sequence with T7 DNA polymerase, ALFRED AUTOREAD Sequencing Kit (Pharmacia Biotech Inc.), an unlabelled primer and M13mp18(+) strand as the DNA template. The results of the DNA sequencing reactions mirror the results of the electrophoresis plots above.

The results are summarized in Table 5.

TABLE 5

| Buffer | pH | Stability of Cy5-dATP Labelling Mix |
|---|---|---|
| 50 mM Citrate | 7.7 | +++ |
| 50 mM Citrate | 6.6 | +++ |
| 50 mM EGTA | 7.8 | ++ |
| 50 mM EDTA | 7.6 | ++++++ |
| 50 mM CDTA | 7.7 | +++ |
| 50 mM isocitrate | 7.7 | +++++ |
| 50 mM isocitrate | 6.4 | ++++ |
| 50 mM phosphate | 7.0 | + |
| Sterile dH$_2$O | ~5.5 | − |

EXAMPLE 6

Cy5-labelled M13 Universal Primer (5'-Cy5-CGA CGT TGT AAA ACG ACG GCC AGT-3'-OH) was resuspended at a concentration of 3 μM in either filtered (10,000 MW cutoff) dH$_2$O or filtered 10 mM isocitrate, pH 6.6. Aliquots of each solution were stored at −20° or +50° for 17 days (as in Example 1). Samples from each of the primers were diluted 1:15 in dH$_2$O or 10 mM isocitrate, pH 6.6, as appropriate, and then mixed with Stop Solution at the ratio of 2 μl primer+5 1 μl dH$_2$O+5 μl Stop Solution. 8 μl from each solution was then loaded and electrophoresed using ALFRED DNA Sequencer. In addition, 2 μl of each primer solution was used directly in a T7 sequencing reaction using the ALFRED AUTOREAD Sequencing Kit, M13mp18(+) strand as the template and ALFRED DNA Sequencer. The results from these ALFRED runs were analyzed and demonstrate (as shown below in Table 6) that isocitrate pH 6.6 buffer acted as a stabilizing agent.

TABLE 6

| Solution Primer was Stored in | −20° C. | +50° C. |
|---|---|---|
| dH$_2$O | + | − |
| Isocitrate, pH 6.6 | + | + |

We claim:

1. A preparation comprising:
    a labelled nucleotide; and
    at least one compound having a Mg$^{2+}$ association constant between $1 \times 10^{-11}$ to $1 \times 10^{-2}$, inclusive, wherein the concentration of the compound is at least 5 mM.

2. The preparation of claim 1, the labelled nucleotide having the formula PM-SM-BASE-SIG wherein PM is a phosphate moiety, SM is a sugar moiety, BASE is a pyrimidine, purine or 7-deazapurine moiety, PM being attached at the 3' or the 5' position of SM when the nucleotide is a deoxyribonucleotide and at the 2', 3' or 5' position when the nucleotide is a ribonucleotide, BASE being attached to the 1' position of SM from the N$^1$ position when BASE is a pyrimidine or the N$^9$ position when BASE is a purine or a 7-deazapurine, and SIG is covalently attached to BASE and wherein SIG represents a detectable moiety.

3. The preparation of claim 2, wherein the at least one compound is selected from the group consisting of citrate, isocitrate, phosphate, EGTA, EDTA, and CDTA.

4. The preparation of claim 3, wherein SIG is selected from the group consisting of fluorophores, and chromophores.

5. The preparation of claim 3, wherein SIG is selected from the group consisting of fluoresceins, carbocyanines, and rhodamines.

6. The preparation of claim 5, wherein SIG is a fluorescein.

7. The preparation of claim 6, wherein the labelled nucleotide is fluorescein-labelled dATP.

8. The preparation of claim 5, wherein SIG is a carbocyanine.

9. The preparation of claim 8, wherein the labelled nucleotide is carbocyanine-labelled dATP.

10. The preparation of claim 1, wherein the labelled nucleotide is covalently attached to at least one nucleoside.

11. The preparation of claim 1, wherein the compound is a carboxylic acid.

12. A method of stabilizing a labelled nucleotide comprising the step of:
    adding to the labelled nucleotide at least one compound having a Mg$^{2+}$ association constant from $1 \times 10^{-11}$ to $1 \times 10^{-2}$, wherein the final concentration of the compound is at least 5 mM.

13. The method of claim 12, comprising the further step of first removing pyrogens from the constituents.

14. The method of claim 13, wherein the removing step is accomplished by filtering.

15. In a polymerization process catalyzed by DNA polymerase, the improvement comprising using the preparation of claim 1 as a substrate.

16. In a polymerization process catalyzed by RNA polymerase, the improvement comprising using the preparation of claim 1 as a substrate.

17. In a polymerization process catalyzed by reverse transcriptase, the improvement comprising using the preparation of claim 1 as a substrate.

* * * * *